(12) United States Patent
Venturini et al.

(10) Patent No.: US 11,701,154 B2
(45) Date of Patent: Jul. 18, 2023

(54) BONE PLATE INTERNAL FIXATOR DEVICE

(71) Applicant: Orthofix S.r.l., Bussolengo (IT)

(72) Inventors: Daniele Venturini, Povegliano Veronese (IT); Federico Vicenzi, Verona (IT)

(73) Assignee: Orthofix S.r.l., Bussolengo (IT)

( * ) Notice: Subject to any disclaimer, the term of this patent is extended or adjusted under 35 U.S.C. 154(b) by 191 days.

(21) Appl. No.: 16/476,815

(22) PCT Filed: Jan. 18, 2018

(86) PCT No.: PCT/EP2018/051237
§ 371 (c)(1),
(2) Date: Jul. 9, 2019

(87) PCT Pub. No.: WO2018/134319
PCT Pub. Date: Jul. 26, 2018

(65) Prior Publication Data
US 2019/0357953 A1 Nov. 28, 2019

(30) Foreign Application Priority Data
Jan. 20, 2017 (IT) .......................... 102017000006369

(51) Int. Cl.
*A61B 17/80* (2006.01)
*A61B 17/86* (2006.01)

(52) U.S. Cl.
CPC ...... *A61B 17/8085* (2013.01); *A61B 17/8057* (2013.01); *A61B 17/8004* (2013.01); *A61B 17/8061* (2013.01); *A61B 17/86* (2013.01)

(58) Field of Classification Search
CPC ............ A61B 17/8004; A61B 17/8085; A61B 17/8057; A61B 17/8052; A61B 17/80
See application file for complete search history.

(56) References Cited

U.S. PATENT DOCUMENTS 8,029,507 B2 10/2011 Green et al.
2004/0111089 A1* 6/2004 Stevens .............. A61B 17/1764
606/907

(Continued)

FOREIGN PATENT DOCUMENTS

EP 1958580 A1 † 8/2008
EP 3045130 A1 † 7/2016
WO 2015187773 A9 † 12/2015

OTHER PUBLICATIONS

International Search Report issued in connection with PCT/EP2018/051237.

(Continued)

*Primary Examiner* — Amy R Sipp
(74) *Attorney, Agent, or Firm* — Akerman LLP

(57) ABSTRACT

The present invention relates to a bone plate internal fixator device (101; 501; 701) for epiphysiodesis, comprising a pair of holding elements (102, 103; 502, 503; 702, 703), each one of the holding elements (102, 103; 502,503; 702, 703) respectively comprising a through hole (104, 105; 504, 505; 704, 705) configured for receiving a respective fixing screw (301) to a bone; the bone plate internal fixator device (101; 501; 701) further comprises a central portion (106; 506; 706) which structurally connects and constrains the holding elements (102, 103; 502, 503; 702, 703) with each other; the central portion (106; 506; 706) is flexible so as to allow flexing of the bone plate (101; 501; 701); each said through hole (104, 105; 504, 505; 704, 705) comprises a threaded surface (108, 109; 508, 509; 708, 709) adapted to couple with a corresponding surface (304) of the respective fixing screw (301); the holding elements (102, 103; 502, 503; 702, 703) and the central portion (106; 506; 706) are provided as a composite structure.

10 Claims, 5 Drawing Sheets

(56) References Cited

U.S. PATENT DOCUMENTS

| | | | |
|---|---|---|---|
| 2005/0065521 A1* | 3/2005 | Steger | A61B 17/80 606/291 |
| 2005/0124992 A1† | 6/2005 | Ferree | |
| 2008/0154312 A1† | 6/2008 | Colleran | |
| 2008/0234676 A1* | 9/2008 | Schulze | A61B 17/8066 606/283 |
| 2010/0004691 A1* | 1/2010 | Amato | A61B 17/808 606/280 |
| 2012/0271358 A1† | 10/2012 | Stevens | |
| 2013/0090695 A1* | 4/2013 | Bernstein | A61B 17/80 606/281 |
| 2015/0045836 A1† | 2/2015 | Luenberger | |
| 2017/0079701 A1 | 3/2017 | Geldwert | |
| 2019/0357953 A1* | 11/2019 | Venturini | A61B 17/8057 |

OTHER PUBLICATIONS

International Preliminary Report on Patentability issued in connection with PCT/EP2018/051237.

* cited by examiner
† cited by third party

BONE PLATE INTERNAL FIXATOR DEVICE

This application is a national phase of PCT/EP2018/051237, filed Jan. 18, 2018, and claims priority to IT 102017000006369, filed Jan. 20, 2017, the entire contents of both of which are hereby incorporated by reference.

FIELD OF THE INVENTION

The present invention relates to an internal fixator device, to be used as a correction means in particular for patients in paediatric age. Such internal fixator device is of the type comprising a bone plate where at least a pair of through holes are obtained for receiving bone fixing screws.

The invention relates in particular, but not exclusively, to a bone plate internal fixator device intended for epiphysiodesis surgery, used to block the natural growth or to correct a limb axis deviation, by limiting the natural growth of the growth plate.

The invention can be usefully applied in the paediatric orthopaedics sector, for example for epiphysiodesis surgery at the ends of deformed long bones of paediatric patients. Therefore, the following description is made referring to the non-limiting use within the scope of such sector.

PRIOR ART

Known techniques for epiphysiodesis surgery provide to limit the development of the growth plate, through the insertion into the bone of devices as: screws arranged longitudinally, staples or bone plates.

Among the techniques used for epiphysiodesis, it is widespread to block the growth plate through the use of a bone plate.

Such bone plate is applied to the bone by means of fixing screws which fasten it respectively to the epiphysis and to the metaphysis at the convex area of the bone deformation. Both the metaphysis and epiphysis portions of the bone plate have at least one through hole adapted to receive one of the aforesaid fixing screws.

In the specific sector of the present invention, problems related to the tolerability for the patient of the above described bone plates are known.

In fact, when the fixing screws of the bone plate are positioned above and below the growth plate, they have to adapt to the curve resulting from the constraint of the bone plate and the variations occurring during the growth.

Particular bone plates are thus known, that are constrained to the bone by means of fixing screws which are susceptible to diverge one another, in order to avoid the exceeding compression of the growth plate and to carefully guide the natural growth process of physis and bones.

One solution disclosed in document U.S. Pat. No. 8,029,507 B2 relates to a plate fixator device for the angular correction of bone deformations, comprising a rotatable hinge arranged transversally in the plate, to enable a relative rotation of the plate under the effect of the load of the fixing screws, so as to support the curve variations occurring during growth.

However, the solution known from document U.S. Pat. No. 8,029,507 B2 constitutes a great encumbrance due to the presence of the hinge, which can reduce the tolerability of the bone plate in particular in regions scarcely covered by soft tissues. Furthermore, the solution known from document U.S. Pat. No. 8,029,507 B2 does not further allow to have an adequate centering reference on the growth plate, for the use of a Kirschner wire for temporarily fixing of the bone plate, according to known surgical techniques.

One further solution disclosed in document US 2004/0111089 A1 refers to a plate fixator device for controlling the bone growth, in particular for correcting bone deformities; this device comprises two fixing screws which are inserted in suitable holes obtained in the bone plate.

In one example disclosed in US 2004/0111089 A1, the head of each fixing screw has a spherical profile for appropriately rotating in an elongated seat obtained in the plate and thus enabling fixing screws to angulate. In order to enable a rotation of the screws stem, it is required a spherical profile of the head of the screw also containing the engagement through which the screw is operated during the screwing operation; therefore, in this known example, the screw head and generally the bone plate are of great encumbrance as regards the height which may reduce the tolerability of the bone plate especially in regions scarcely covered by soft tissues.

In further examples described in US 2004/0111089 A1, it is provided to make a central connection between the bone plate holes be flexible, so that the fixing screws are capable of moving following the movement of bone sections. Examples of flexible connections known from US 2004/0111089 A1 provide: a midsection of the plate made of flexible material, one plate made of fabric with rigid material surrounding the openings, or the use of a flexible band to surround the fixing screws instead of a plate, eventually providing it with a crimping in the middle.

Even though the implants known in the art partly improve the tolerability of the bone plate for the patient, enabling a relative rotation of the plate ends so that the fixing screws can support the variations occurring during the growth, they have however some limits.

First of all, an exceeding flexibility of the bone plate can lead to problems in fixing it in the desired position.

Furthermore, even if they follow the movement of bone sections, flexible bone plates can in any case be of such an encumbrance, especially as regards the height, as to encourage the burst of an inflammatory process in the soft tissue.

In addition, a flexible bone plate can be too delicate, with the risk of breaking when submitted to the stresses caused by the bone growth.

And again, the configurations of the flexible bone plate adopted by the known art can lead to a crushing of the growth plate, thus further reducing the tolerability of the implant.

AIMS OF THE INVENTION

Aim of the present invention is solving problems of the prior art.

One particular aim of the present invention is providing a bone plate implant that can be optimally fixed to the bone.

One further particular aim of the present invention is providing a bone plate implant that is better tolerated by the patient, even when it is applied in anatomic regions scarcely covered by soft tissues.

One further particular aim of the present invention is providing a bone plate implant that is robust and suitable for epiphysiodesis applications.

One further particular aim of the present invention is presenting a bone plate implant that does not interfere with the growth plate.

SUMMARY OF THE INVENTION

One idea of solution underlying the present invention is providing a bone plate internal fixator device for epiphysiodesis, comprising a pair of holding elements, each one respectively comprising a through hole for receiving a respective fixing screw to a bone. The bone plate internal fixator device further comprises a central portion which structurally connects and constrains the holding elements with each other, the central portion being flexible so as to allow flexing of the bone plate. Each one of the through holes comprises a threaded surface that is adapted to couple with a corresponding surface of the respective fixing screw. The holding elements and the central portion are provided as a composite structure.

Advantageously, the threaded surface of the through holes allows to realise an improved coupling with the fixing screws, so that it can be implanted with more precision on the bone and at the same time realise a structurally more stable assembly.

Furthermore, the presence of the threaded surface of the through holes enables to realise a coupling between the head of the fixing screws and the bone plate with less encumbrance as regards the height, and with no projecting portions, thus resulting more tolerable in particular when the implant is applied in anatomic regions scarcely covered with soft tissues.

Also, while the flexible central portions allow for a wide range of angular opening of the bone plate, during evolution of the epiphysiodesis surgery, the fixing screws always remain co-planar to the plane which encompasses the flexing angle, and the axis of each fixing screw remains substantially perpendicular to the respective holding element.

Also, the structure of the internal fixator device with threaded-surface holes generally results to be more robust and therefore suitable for epiphysiodesis applications, wherein the plate is submitted to even relevant stresses.

Furthermore, in order to improve tolerability, the internal fixator device is preferably characterised by a central portion which is raised with respect to the bottom surfaces of the holding elements, so as to limit pressures on the bone physis and avoid the lateral crushing of the growth plate.

Further features and advantages of the bone plate internal fixator device of the present invention will be more apparent from the hereinafter description of exemplary and non-limiting embodiments.

BRIEF DESCRIPTION OF THE DRAWINGS

The present description refers to the enclosed drawings, wherein.

In different figures, analogous elements will be indicated by analogous reference numbers.

DETAILED DESCRIPTION OF THE PREFERRED EMBODIMENTS

Figure 1:
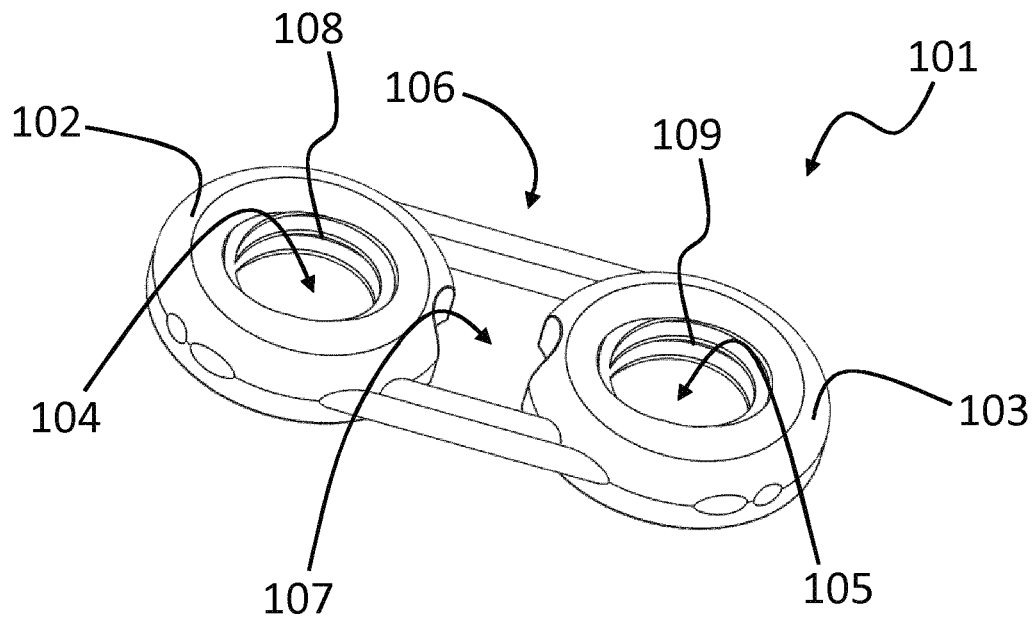
FIG. 1 shows a perspective and schematic view of one embodiment of a bone plate internal fixator device according to the present invention.

With reference to the example of FIG. 1, it is schematically illustrated one first embodiment of a bone plate internal fixator device 101.

The fixator device according to the present invention is particularly adapted to, but not exclusively limited to, be used in orthopaedics for epiphysiodesis surgery i.e. treatment of long bones malformations, in particular for paediatric and/or adolescent age patients, through the applications of the fixator device across of the physis of such bones.

The internal fixator device 101 comprises one first holding element 102 and one second holding element 103, which respectively comprise a through hole 104 and 105, which are configured to receive one respective fixing screw when the fixator device is implanted to the bone.

Holding elements 102 and 103 are preferably constituted of a rigid and biocompatible material (e.g. titanium) and have a substantially circular shape, with uniform thickness.

Holding elements 102 and 103 are structurally interconnected by a central portion 106 which constrains holding elements 102 and 103 with each other, realising a bone plate structure.

The holding elements 102 and 103, and the central portion 106 are provided as a composite structure.

A "composite structure" is a structure made of at least two different materials or comprising at least two different material configurations (i.e. solid metal and braided metal), which exhibit different mechanical properties.

In other words, the holding elements and the central portion of the internal fixator device according to the invention, are made at least partially of two materials which are different or differently arranged.

In general, at least part of the holding elements and the central portion are originally provided as independent components of the internal fixator device. Such independent components are connected to form the composite structure during manufacturing of the internal fixator device.

The central portion 106 is flexible so as to enable a relative flexing between holding elements 102 and 103, i.e. flexing of the bone plate. At the same time, the central portion 106 has tensile strength ensuring the structural integrity of the bone plate during the tensile-flexion phase.

The flexing of the bone plate corresponds to a relative rotation of the individual planes of holding elements 102 and 103, which result to be adapted to allow the fixing screws to angulate, so as to support the variations of angle occurring during the bone growth, providing an improved tolerability of the implant in epiphysiodesis surgery.

In particular, the flexible central portion 106 allows for a wide range of angular opening of the holding elements 102 and 103 of the internal fixator device 101. In this way, during bone growth in an epiphysiodesis surgery, the variations of angle allowed by the internal fixator device 101 can be further improved.

The central portion 106 preferably comprises one through hole 107, which is configured to allow insertion of a wire guide (not shown) so as to use a Kirschner wire for centering the bone plate during the implantation, in such a way that the central portion is positioned correctly across of the growth plate.

When considering holding elements 102 and 103, each one of them comprises one respective threaded surface 108 and 109 realised inside the through holes 104 and 105 respectively.

In particular, preferably, the through holes 104 and 105 are substantially cylindrical and the threaded surfaces 108 and 109 are the inner lateral surfaces of the cylindrical holes. In other words, the through holes 104 and 105 comprise a threaded cylindrical hole, which develops coaxially with inlet and outlet diameters substantially equal to each other.

Such threaded surfaces 108 and 109, as will be further described, are adapted to couple with respective correspondingly threaded surfaces of fixing screws, to realise the implant structure.

In particular, the through holes 104 and 105 the threaded surfaces 108 and 109 are configured such that the fixing screws always remain co-planar to the plane which encompasses the flexing angle, and the axis of each fixing screw remains substantially perpendicular to the respective holding element 102 or 103.

Figure 2:
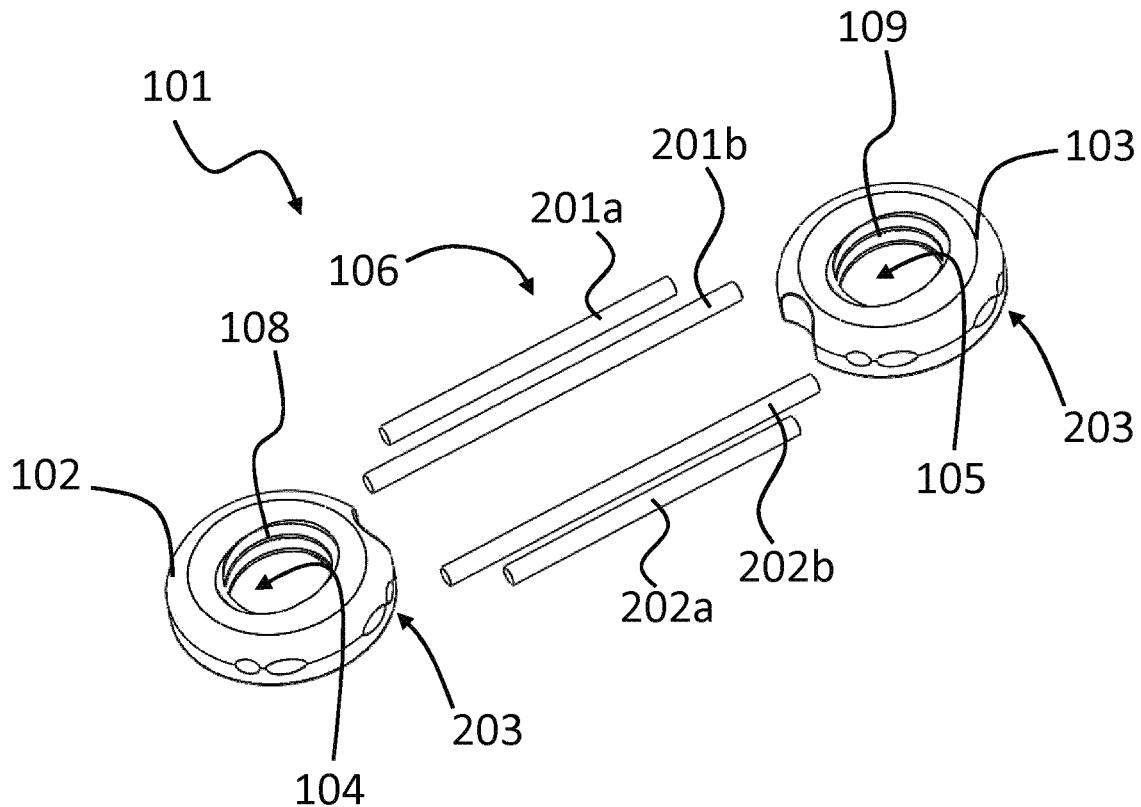
FIG. 2 shows a perspective and schematic view of the fixator device of FIG. 1, in disassembled configuration and from a different point of view.

In FIG. 2 the fixator device 101 is visible, in disassembled configuration, so as to appreciate the particular embodiment of the flexible central portion 106.

In this embodiment, the flexible central portion comprises four resilient elements 201a, 201b, 202a, 202b arranged in pairs to constrain holding elements 102 and 103 between each other. In other possible embodiments, a different number of resilient elements could be provided, for example one single pair.

Resilient elements 201a, 201b, 202a, 202b comprise metallic wires or cables which are constrained with each own end to one respective of the holding elements 102 and 103.

The number of metallic wires or cables, their size and structure can be calibrated according to the flexing elasticity and the tension strength desired for the bone plate.

The constraint or blocking of the wires in the holding elements can obtained by welding, plastic deformation (crimping), or other mechanical constraints. In particular, the constraint in the holding elements occurs by means of passing metal wires or cables inside suitable holes 203 realised tangentially in holding elements 102 and 103.

In general, by the term "wires" it is meant an elongated wire-like element, of any section but preferably circular; such "wires" can be made of uniform and solid material or of material arranged in strand or other composite configurations.

In general, by the term "cables" it is meant an elongated wire-like element, with preferably circular section, made of uniform material or of material arranged as a strand, in particular of metallic or non-metallic material.

Preferably, resilient elements 201a, 201b, 202a, 202b are arranged symmetrically with respect to a longitudinal axis of the fixator device 101, that is to say, a longitudinal axis ideally connecting the centres of holes 104 and 105.

Therefore, resilient elements 201a, 201b, 202a, 202b represent one particular embodiment of the already described flexible central portion 106.

Figure 3:
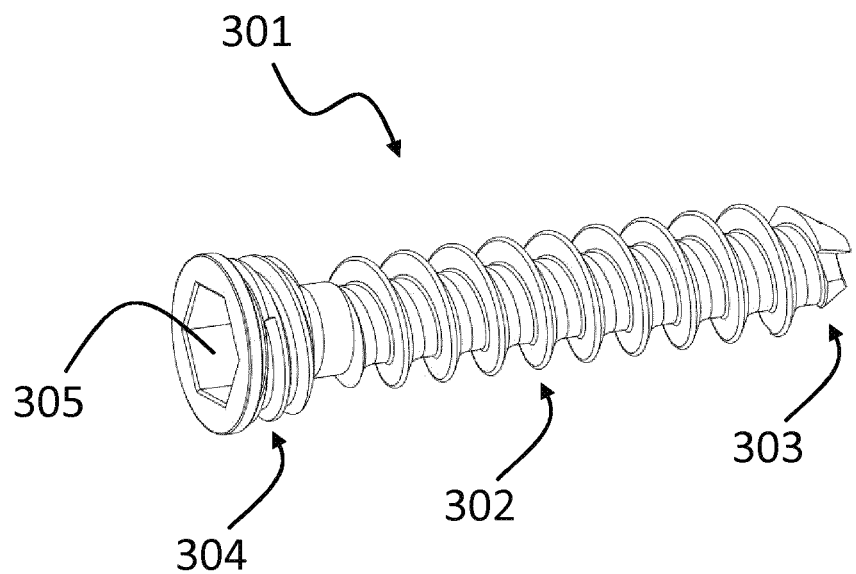
FIG. 3 shows a perspective and schematic view of one fixing screw for a bone plate internal fixator device according to the present invention.

FIG. 3 shows one embodiment of a fixing screw 301, specifically configured for use in a bone plate internal fixator device according to the present invention.

Fixing screw 301 is preferably constituted of a rigid and biocompatible material (e.g. titanium).

Fixing screw 301 comprises a threaded stem 302, preferably comprising a triangular-profile thread. Fixing screw 301 further comprises a tip 303, preferably of the self-tapping type. Fixing screw 301 further comprises a head 304, provided with a thread on its own external cylindrical surface. The head 304 is provided with proper grasping means 305, for instance a hexagonal recess for screwing the fixing screw 301 into the bone.

The head thread 304 is adapted to couple with the threaded surfaces 108 and 109 of the internal fixator device, which are correspondingly threaded, to realise the implant structure.

Preferably, the threaded surfaces 108 and 109, and therefore the corresponding head thread 304 too, provide a two-starts thread, to simplify the screwing during the implant application and to allow the advancement equal to the pitch of the thread on the stem 302.

Preferably, the thread of stem 302 of the fixing screws 301 has a thread pitch which is different from the thread pitch of the surfaces 108 and 109; this further contributes to simplify the application of the implant. In particular, the thread of stem 302 has a pitch which is twice as compared to the thread pitch 304, to enable a suitable advancement and a more accurate application in the terminal screwing part, when the head thread 304 engages with the thread 108 or 109 of the bone plate.

Figure 4:
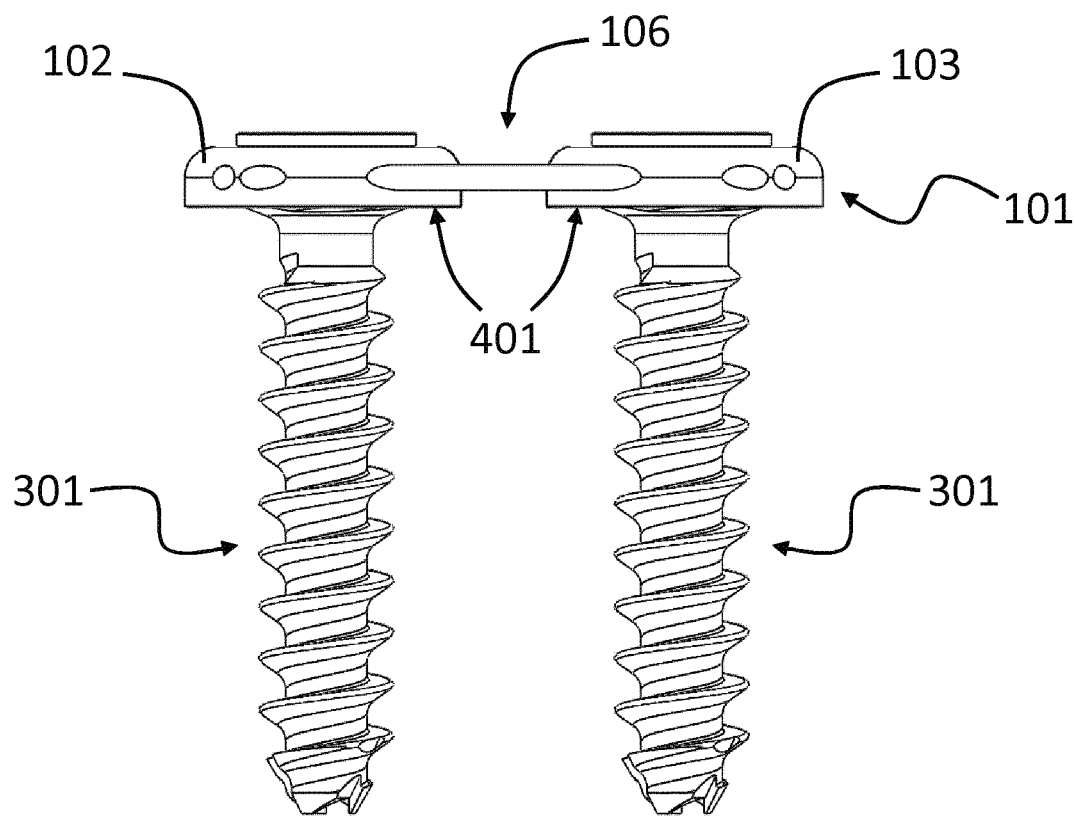
FIG. 4 shows a side view of an implant comprising one pair of fixing screws of FIG. 3 and the bone plate internal fixator device of FIG. 1.

In FIG. 4 it is shown an implant for epiphysiodesis according to the present invention, that is an assembled kit which comprises a pair of fixing screws 301 and a bone plate internal fixator device 101. Fixing screws are applied, through the thread of the head 304, to the respective threads 108 and 109 in the through holes 104 and 105 of holding elements 102 and 103.

By means of the fixing screws 301, holding elements 102 and 103 are thus adapted to be fixed, through the assembling screws, respectively to the epiphysis and the metaphysis of a long bone of a paediatric-age patient, for example a bone having an angular deformation to be corrected through the application of the fixator device 101.

The central portion 106, being flexible, allows the stems of the screws 301 to angulate, being well tolerated by the patient even in the various phases of the bone growth.

The bone plate internal fixator device 101, as described, is configured such that each one of the fixing screws 301 always remain co-planar to the plane to the respective holding element 102 or 103, thus avoiding unwanted stresses on the internal fixator device 101, and improving tolerability of the implant.

The threaded surfaces 108 and 109 of holding elements 102 and 103 are thus configured to solidly constrain each one of the holding elements 102 and 103 with the respective fixing screw 301, so as to realise a bone plate assembly that is flexible exclusively in the central portion 106.

The threaded coupling between the head of the fixing screws 301 and holding elements 102 and 103 enables to obtain an improved constraint, so that the internal fixator device 101 can be implanted with greater precision and is structurally more stable.

As it can be appreciated in FIG. 4, the presence of the threaded surface of the through holes of holding elements 102 and 103 enables to realise a coupling between the head of the fixing screws 301 and the bone plate 101 which is less encumbering as regards the height, without projecting portions. In fact, according to the present invention it is not necessary that the fixing screw 301 "abuts" with the bottom head surface on the holding elements, but it is sufficient that the respective threads of the screws heads and of the through holes engage with each another, realising a stable assembly.

The internal fixator device according to the present invention is thus more tolerable, in particular when the implant is applied in anatomic regions scarcely covered by soft tissues.

Furthermore, the structure of the internal fixator device 101 with threaded surface holes, is in general more robust and adapted to endure stresses in epiphysiodesis applications.

As it can be appreciated in FIG. 4, in order to improve tolerability, the internal fixator device comprises a central portion 106 which is raised with respect to bottom surfaces 401 of the holding elements 102 and 103, provided to be placed in contact with the bone surface. Thereby, it is possible to limit pressures on bone physis and thus avoid laterally crushing the bone plate.

In other words, the internal fixator device 101 is substantially flat, but the central portion 106 is raised with respect to bottom surfaces 401 of holding elements 102 and 103, which are configured to face towards the stem of the fixing screws 301. Thereby, it is possible to limit pressure on the bone physis.

Figure 5:
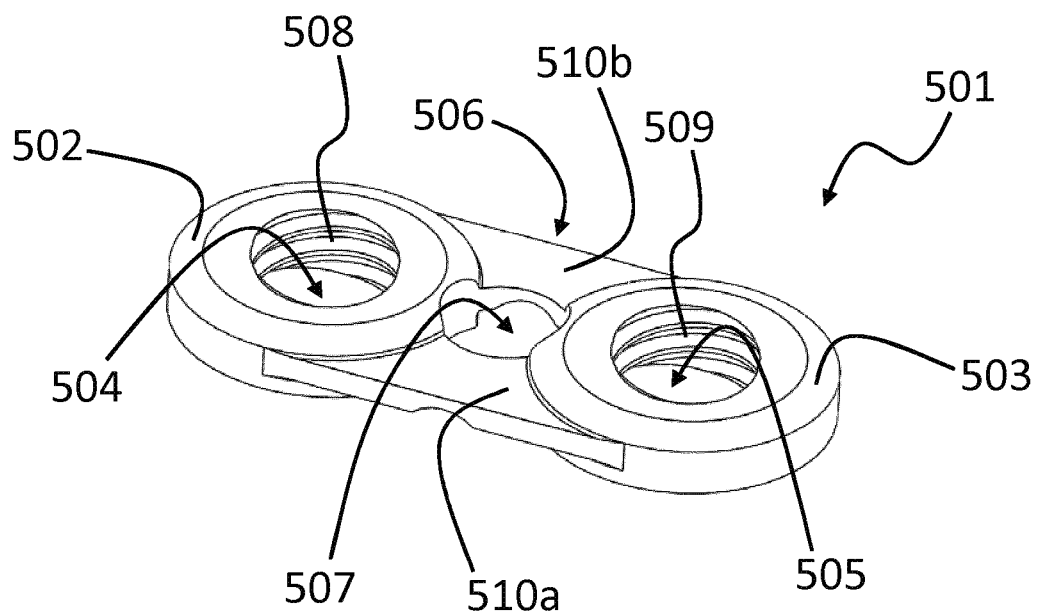
FIG. 5 shows a perspective and schematic view of one second embodiment of a bone plate internal fixator device according to the present invention.

With reference to the example of FIG. 5, it is schematically illustrated one second embodiment of a bone plate internal fixator device 501.

The internal fixator device 501 comprises one first holding element 502 and one second holding element 503, each one comprising a respective through hole 504 and 505, similar to the elements already described with reference to the internal fixator device 101.

The central portion 506 structurally connecting and constraining holding elements 502 and 503 between each other, is flexible so as to allow flexing of the bone plate.

The central portion 506 preferably comprises one central through hole 507, which is configured to enable the insertion of a wire guide (not shown) so as to use a Kirschner wire.

Through holes 504 and 505 of holding elements 502 and 503 each comprise one respective threaded surface 508 and 509, respectively.

Such threaded surfaces 508 and 509 are configured to couple with a corresponding surface of the head of the fixing screw 301, similarly to what described with reference to the internal fixator device 101.

The central portion 506 comprises one pair of bridge elements 510a and 510b, made of flexible plastic material, separated between each other by the through hole 507. In one alternative embodiment, the central hole 507 may be omitted resulting in one single bridge element.

In general, the pair of bridge elements 510a e 510b is made of flexible plastic material, and is symmetrically arranged with respect to a longitudinal axis of the internal fixator device 501.

In general, a plastic material having suitable resistance and biocompatibility characteristics is polyether-ether-ketone (PEEK).

Preferably, also holding elements 502 and 503 are made of plastic material, being more preferably made in a piece with bridge elements 510a and 510b, in one single mould.

Advantageously, plastic material elements can be more easily obtained through moulding processes, making these embodiments cheaper than embodiments comprising metallic material elements.

Furthermore, plastic materials portions are radiolucent and, in addition to being biocompatible, they also ensure suitable mechanical strength and resilience.

In one alternative embodiment, holding elements 502 and 503 can be made of metallic material connected to bridge elements by suitable bonding.

The embodiment of the fixing device 501 thus envisages different elements for providing the flexible central portion 506, keeping at the same time unchanged the functioning of the bone plate with respect to what already described for the fixator device 101.

Figure 6:
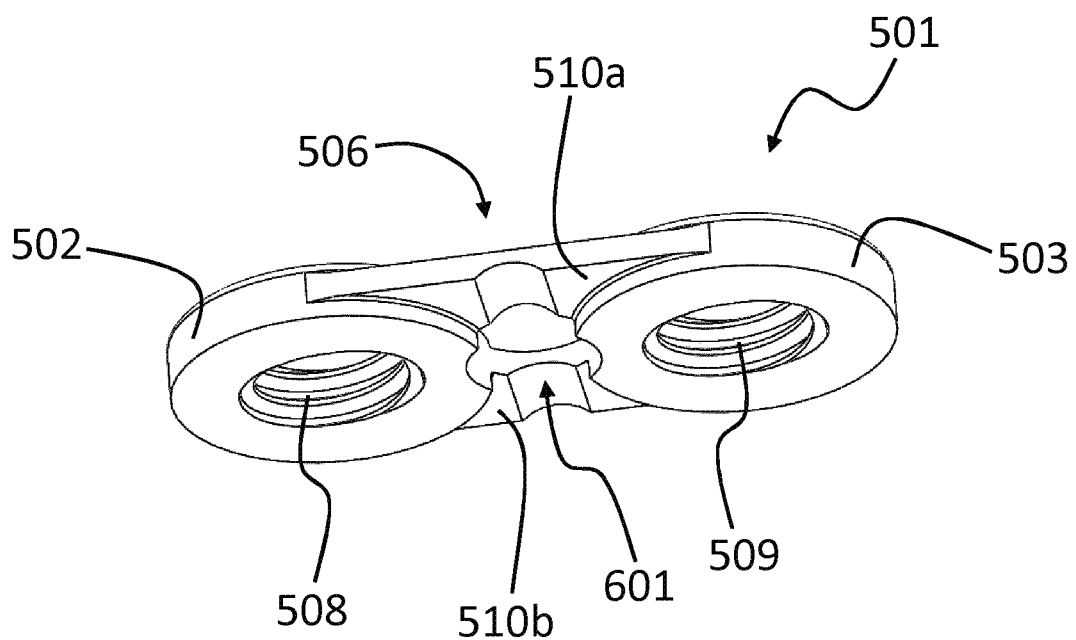
FIG. 6 shows a perspective and schematic view of the fixator device of FIG. 5, viewed from below.

FIG. 6 shows the fixator device 501 viewed from below. In this view, it is possible to appreciate that the central portion 506 comprises one recess 601 on the bottom surface, which enables to further raise the central portion 506 and to generate one preferential bending axis of the plate 501. Thereby, the raised central portion 506 is further adapted to limit the pressures on the bone physis, when the fixator device 501 is implanted.

Figure 7:
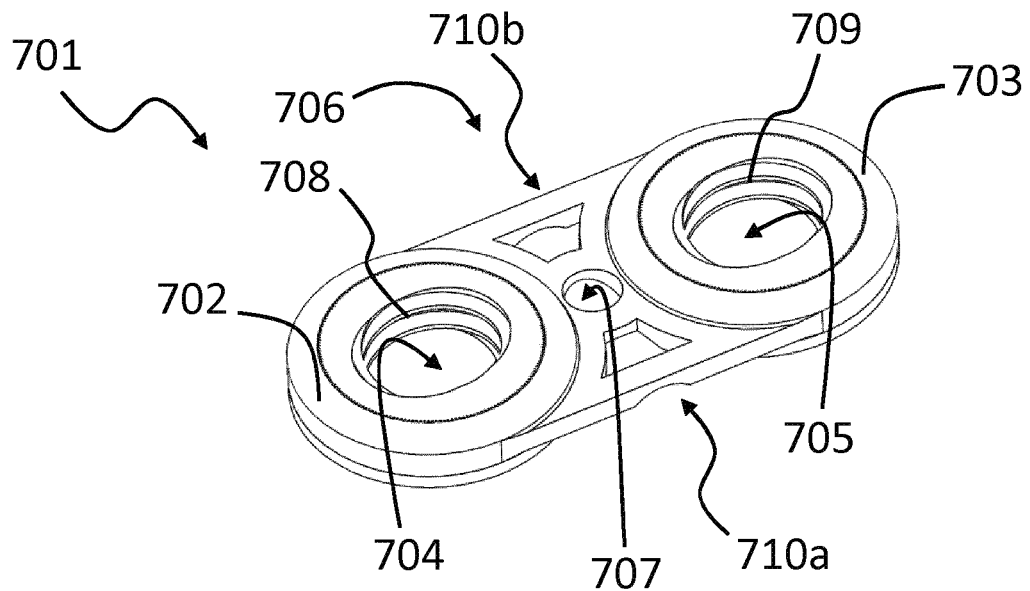
FIG. 7 shows a perspective and schematic view of one third embodiment of a bone plate internal fixator device according to the present invention.

With reference to the example of FIG. 7, it is schematically illustrated one third embodiment of a bone plate internal fixator device 701.

The internal fixator device 701 comprises one first holding element 702 and one second holding element 703, comprising respective through holes 704 and 705. The central portion 706 structurally connecting and constraining holding elements 702 and 703 between each other, is flexible so as to allow flexing of the bone plate. The central portion 706 preferably comprises one central through hole 707, which is configured to enable the direct passage of a Kirschner wire, preferably without the aid of a guide wire.

Through holes 704 and 705 of holding elements 702 and 703 each comprise one respective threaded surface 708 and 709, respectively. Such threaded surfaces 708 and 709 are configured to couple with a corresponding surface of the head of the fixing screw 301, similarly to what described with reference to the internal fixator device 101.

The central portion 706 comprises one pair of bridge elements 710a and 710b, which, among others, realise the geometry of the through hole 707. In general, bridge elements 710a and 710b are arranged symmetrically with respect to a longitudinal axis of the internal fixator device 701.

The embodiment of fixator device 701 is therefore distinguished from the fixator device 101 or 501 due to a different supporting structure.

Figure 8:
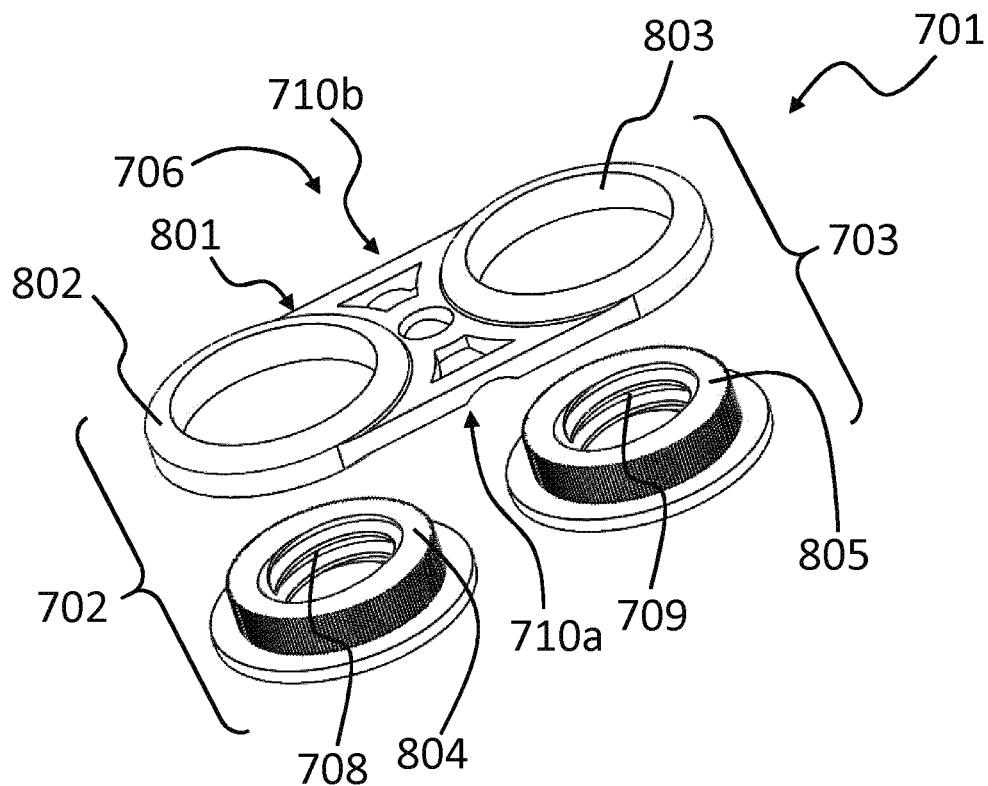
FIG. 8 shows the fixator device of FIG. 7, in a partially disassembled configuration.

As visible in FIG. 8, the partially disassembled fixator device 701 comprises one supporting frame 801 made in one piece of plastic material. Thereby, it is realised a perimetric portion 802 and 803 which is part of the structure of each one of the holding elements; thereby, the perimetric portion 802 and 803 of the holding elements is made in a piece with bridge elements 710a and 710b.

The supporting frame 801 is associated to a pair of annular elements 804 and 805, respectively implantable in the perimetric portions 802 and 803.

Annular elements 804 and 805 are preferably made of stronger material, such as a metallic material, and include already described threaded surfaces 708 and 709.

Thereby, it is realised a threaded coupling between screws 301 and threaded surfaces 708 and 709 of the annular elements 804 and 805 which is structurally more robust, leaving the frame 801 the task to contribute to the flexibility of the central portion 706.

The fixator device 701 thus obtained enables to improve size tolerance and implementation quality, leaving unchanged the above described optimal functionalities.

The engraftment of annular elements 804 and 805 in the respective seats obtained in the perimetric portions 802 and 803 preferably occurs through appropriately knurled surfaces, to avoid the undesired rotation of annular elements subject to the tightening torque of fixing screws 301.

Figure 9:
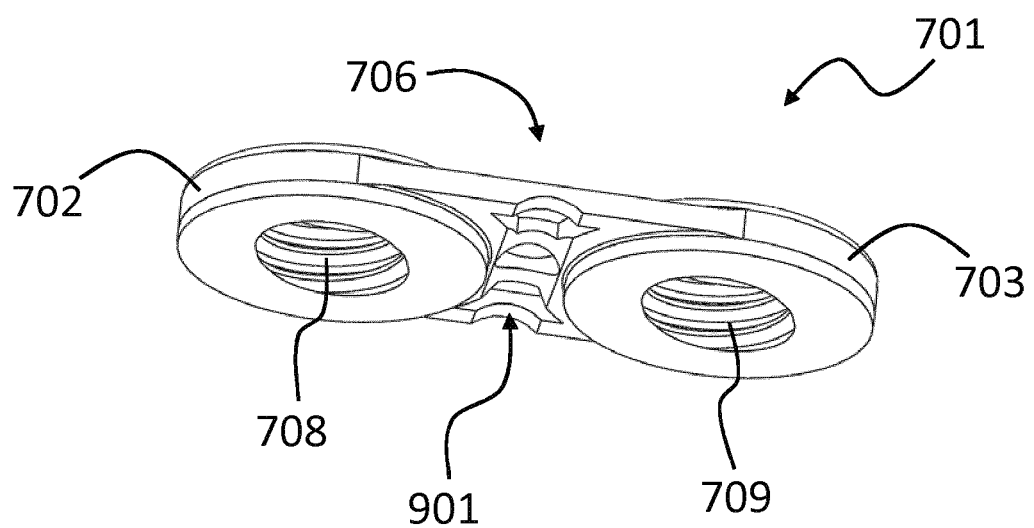
FIG. 9 shows a perspective and schematic view of the fixator device of FIG. 7, viewed from below.

FIG. 9 shows the fixator device 701 viewed from below. In this view, it is possible to appreciate that the central portion 706 comprises one recess 901 on the bottom surface, which enables to further raise the central portion 706. Thereby, as already described, the raised central portion 706 limits pressures on the bone physis.

In general, it is possible to appreciate how in all embodiments, the internal fixator device advantageously has lower and upper perimetric edges which are rounded for a higher tolerability.

In particular, generally, embodiments provide bone plate internal fixator devices that are substantially flat, with an oblong shape without narrowing. In this sense, herein described embodiments differ from typical "eight plates" known in the art.

Flexible central portions of internal fixator devices according to the present invention provide members, such as resilient elements or bridge elements, which are arranged tangentially with respect to the perimeter of holding elements. Thereby, though ensuring a proper flexibility of the bone plate, it is provided an improvement of mechanical stability. Furthermore, the portions of the oblong shape without narrowing enable an improved manipulation by the surgeon during the application of the implant.

In conclusion, it is synthetically described a use of the bone plate internal fixator device of the present invention, referring to FIG. 4.

Once having made a relatively non-invasive incision in the skin and in the flesh of the patient to be submitted to the implantation, the fixator device 101 is placed across of the physis, so that the two holding elements 102 and 103 are in contact respectively with the epiphysis and metaphysis of the bone to be treated.

A fixing wire inserted into the physis cartilage through the central through hole in the flexible central portion 106 allows to keep in position, though temporarily, the fixator device 101.

Fixing screws 301 are at first inserted into the through holes, so as to penetrate in the corresponding portions of epiphysis and metaphysis of the bone until the head 304 reaches and engages with the threaded surface of through holes.

During the growth of the physis tissue, fixing screws 301 undergo a dragging action which determines an angular opening over the whole treatment, that is tension and flexing of the bone plate of the internal fixator device 101.

By enabling flexing of the bone plate 101, an angular opening of fixing screws 301 is also enabled, following the bone growth for the whole duration of treatment.

Advantageously, the bone plate internal fixator device according to the present invention, has a flat conformation and uniform thickness without projections so as to avoid friction areas with soft tissue surrounding the implant.

At the same time, advantageously, the bone plate internal fixator device according to the present invention, has an increased structural stability thanks to the constraint between the threaded surfaces of the through holes and the screws heads, resulting in a better performing implant and able to follow curve variations due to the growth of the bones.

Still advantageously, the fixator device conformation has a rational structure and adapted to be manufactured with qualitatively good tolerances.

The bone plate according to the invention solves the technical problem and achieves several advantages, among which ensuring the complete bone deformation correction through one single epiphysiodesis surgery.

What is claimed is:

1. A bone plate internal fixator device for epiphysiodesis by application across a bone physis for limiting natural growth of a growth plate of a long bone, in particular in paediatric and/or adolescent age patients, the bone plate internal fixator device comprising:
   a first holding element comprising a respective first through hole configured for receiving a respective first fixing screw to the long bone;
   a second holding element comprising a respective second through hole configured for receiving a respective second fixing screw to the long bone;
   a central portion structurally connecting and constraining said first holding element with said second holding element;
   wherein said central portion comprises at least one bridge element made of flexible plastic material configured to allow flexing of said bone plate internal fixator device prominently in said central portion;
   wherein said first through hole and said second through hole are configured for solidly constraining said first holding element and said second holding element with said respective fixing screws;
   wherein said bone plate internal fixator device is substantially flat;
   wherein said central portion comprises an upper surface which is flat;
   wherein said first holding element and said second holding element respectively comprise bottom surfaces which are flat;
   wherein said central portion comprises a bottom surface which is raised with respect to the bottom surfaces of the holding elements, so as to limit pressure on the bone physis; and
   wherein said central portion further comprises one arched recess on the bottom surface thereof, said arched recess locally reducing a cross section of said at least one bridge element and defining a preferential bending axis for flexing of the bone plate internal fixator device.

2. The bone plate internal fixator device for epiphysiodesis according to claim 1, wherein said first through hole and said second through hole comprise respective threaded surfaces adapted to couple with corresponding surfaces of said respective fixing screws.

3. The bone plate internal fixator device for epiphysiodesis according to claim 1, wherein said first through hole and said second through hole are substantially cylindrical.

4. The bone plate internal fixator device for epiphysiodesis according to claim 3, wherein inner lateral surfaces of said substantially cylindrical through holes are threaded.

5. The bone plate internal fixator device for epiphysiodesis according to claim 1, wherein said first holding element, said second holding element and said at least one bridge element are made in one plastic piece.

6. The bone plate internal fixator device for epiphysiodesis according to claim 5, the device made of polyether-ether-ketone (PEEK).

7. The bone plate internal fixator device for epiphysiodesis according to claim 1, wherein said central portion further comprises one central through hole configured to enable insertion of a wire guide.

8. The bone plate internal fixator device for epiphysiodesis according to claim 7, wherein said central portion comprises a pair of bridge elements symmetrically arranged with respect to a longitudinal axis of the bone plate internal fixator device.

9. An epiphysiodesis kit comprising:
a bone plate internal fixator device for epiphysiodesis by application across a bone physis for limiting natural growth of a growth plate of a long bone, in particular in paediatric and/or adolescent age patients, the bone plate internal fixator device comprising a first holding element, a second holding element, and a central portion structurally connecting and constraining said first holding element with said second holding element;
two fixing screws configured to attach to a bone epiphysis and to a bone metaphysis of the long bone, respectively;
wherein said first holding element and said second holding element comprise a first through hole and a second through hole each configured for receiving one of said two fixing screws;
wherein said central portion comprises at least one bridge element made of flexible plastic material configured to allow flexing of said bone plate internal fixator device prominently in said central portion;
wherein said first through hole and said second through hole are further configured for solidly constraining said first holding element and said second holding element with said respective two fixing screws;
wherein said bone plate internal fixator device is substantially flat;
wherein said central portion comprises an upper surface which is flat;
wherein said first holding element and said second holding element respectively comprise bottom surfaces which are flat;
wherein said central portion comprises a bottom surface which is raised with respect to the bottom surfaces of the holding elements, so as to limit pressure on the bone physis; and
wherein said central portion further comprises one arched recess on the bottom surface thereof, said arched recess locally reducing a cross section of said at least one bridge element and defining a preferential bending axis for flexing of the bone plate internal fixator device.

10. The epiphysiodesis kit of claim 9, wherein each one of said two fixing screws comprises a head which is threaded on its outer surface, said head being configured for coupling with a respective threaded surface of said respective first through hole and second through hole.

* * * * *